United States Patent [19]
Juster et al.

[11] 3,934,721
[45] Jan. 27, 1976

[54] PACKAGED CATHETER ARRANGEMENT

[75] Inventors: Robert W. Juster, St. Louis, Mo.; William E. Patton, North Canton, Ohio

[73] Assignee: Affiliated Hospital Products, Inc., St. Louis, Mo.

[22] Filed: Feb. 15, 1973

[21] Appl. No.: 332,584

Related U.S. Application Data
[63] Continuation of Ser. No. 149,990, June 4, 1971, abandoned.

[52] U.S. Cl. .............................. 206/364; 128/349 R
[51] Int. Cl. ..................... A61b 19/02; A61m 25/00
[58] Field of Search ........ 128/348, 349 R, 350, 351; 206/63.2 R, 364

[56] References Cited
UNITED STATES PATENTS

| | | | |
|---|---|---|---|
| 2,863,453 | 12/1958 | Gewecke | 128/227 |
| 3,035,691 | 5/1962 | Rasmussen et al. | 206/63.2 R |
| 3,112,031 | 11/1963 | Stewart | 206/63.2 R |
| 3,169,527 | 2/1965 | Sheridan | 128/349 R |
| 3,203,545 | 8/1965 | Grossman | 206/63.2 R |
| 3,215,265 | 11/1965 | Welin-Berger | 206/63.2 R |
| 3,606,001 | 9/1971 | Talonn et al. | 206/63.2 R |
| 3,750,875 | 8/1973 | Juster | 128/349 R |

*Primary Examiner*—Dalton L. Truluck
*Attorney, Agent, or Firm*—Reginald F. Pippin, Jr.

[57] ABSTRACT

A packaged catheter arrangement having a soft and pliable latex rubber catheter for body orifice use and having its shaft slidably removably disposed within a relatively rigid tube sheath of plastic to form a catheter handling assembly which is enclosed as a unit within a peripherally sealed peel-apart dual sheet overpackage. The tube sheath is sealed closed at one end and the catheter preferably has a pre-lubrication coating on its insertion shaft and enclosed within the closed-ended tube sheath.

9 Claims, 6 Drawing Figures

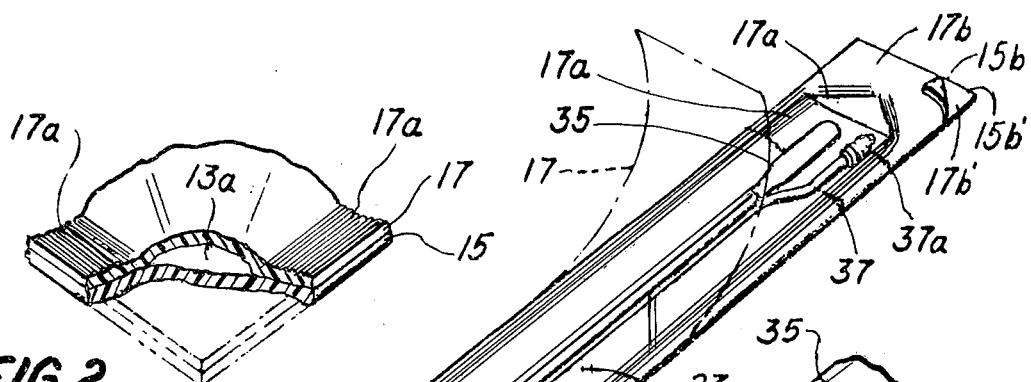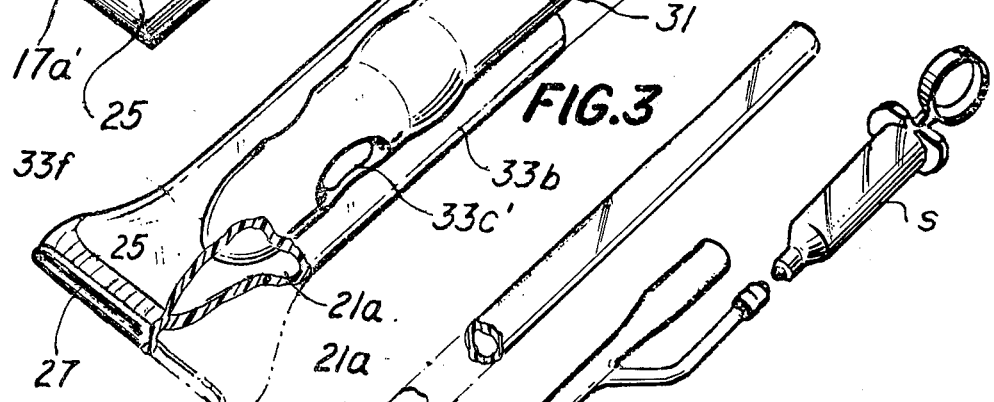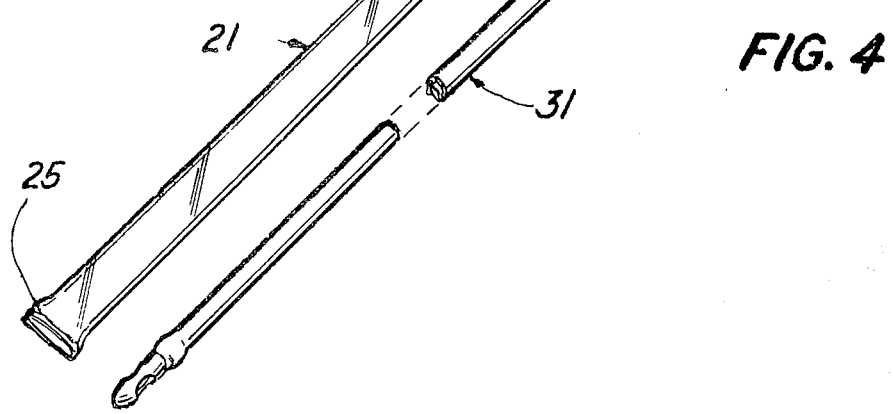

PACKAGED CATHETER ARRANGEMENT

This application is a continuation of copending application Ser. No. 149,990, filed June 4, 1971, now abandoned.

This invention relates to an improved packaged catheter arrangement, and particularly to a packaged catheter arrangement which enables opening of the package and subsequent aseptic handling of the catheter in a mann that substantially reduces the likelihood of possible contamination of the catheter shaft prior to insertion into a patient.

It is conventional practice to furnish catheters in individual packages, so as to enable the catheters to be maintained in sterile condition until the desired time of use. Various packaging arrangements have been proposed and used for this purpose. It is a feature of the present invention to provide an improved packaging arrangement for point-of-use opening, and which enables subsequent rehandling of the catheter on a subassembly basis after opening of the overpackage, without seriously endangering the sterility of the catheter shaft.

It is a further feature of the invention to provide a package arrangement for catheters in which a catheter is reliably held in an extended position within a longitudinal overpackage, through the medium of a relatively rigid tube sheath which encompasses the insertion shaft of the catheter, thereby preventing the catheter from sliding down in the package and possibly kinking, and also making the catheter much easier to handle after removal from the overpackage, by grasping the tube sheath rather than the insertion shaft of the catheter.

Still a further feature is the provision of a catheter package arrangement which enables the packaging and storing until opening for use, of a catheter having a pre-lubricated shaft, while substantially obviating the normal likelihood of lubrication bleeding and staining of the outer package, and which further holds the catheter in a generally straight and unkinked packaged condition until removed for use, and which also enables controlled withdrawal of the catheter from a protective handling portion of the package arrangement.

Still other objects, features and attendant advantages will become apparent to those skilled in the art from a reading of the following detailed description of a preferred embodiment constructed in accordance with the invention, taken in conjunction with the accompanying drawings, wherein:

FIG. 1 is a perspective view illustrating a preferred embodiment of the invention.

FIG. 2 is a fragmentary view of one end corner of the package of FIG. 1.

FIG. 3 is an enlarged view of the assembled catheter and sheath assembly of FIG. 1.

FIG. 4 is an exploded view of the tubular sheath and catheter of FIGS. 1 and 3, together with a conventional syringe for catheter retention ballon inflation and deflation.

Figure 5:
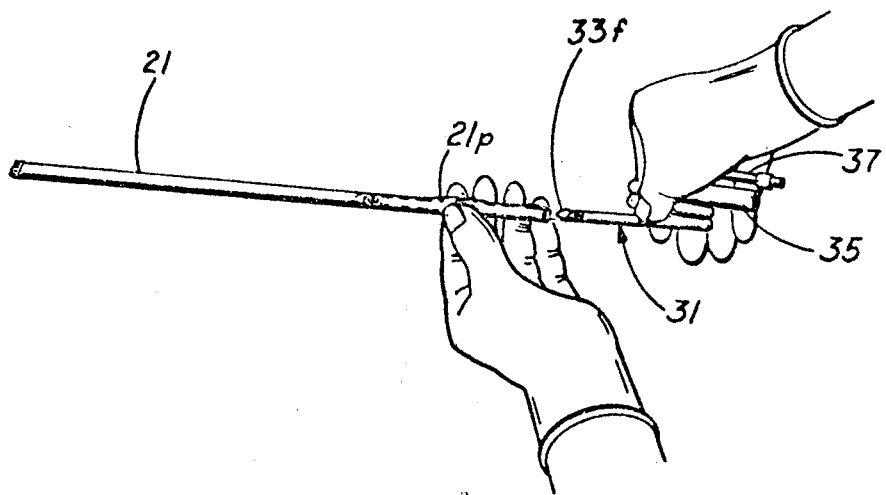
FIG. 5 illustrates the removal of the catheter from the tube sheath of FIG. 1, and the handling of the catheter by an operator during this removal operation.

In the preferred embodiment as illustrated in FIG. 1, a catheter, generally indicated at 31, is inserted with its shaft 33 extending through a major extent of the length of a relatively rigid tube sheath 21, and the catheter 31 and tube sheath 21 are in turn contained within a peripherally sealed sterile zone pocket formed within an overpackage 13, thereby forming a complete package 11 of removable catheter and tube sheath unit 31, 21 contained within a sealed overpackage container 13.

The catheter 31 is merely an illustrative form of catheter, and may be of any suitable or desired catheter construction having a Y or other divergent fluid passage arm configuration. In the illustrative catheter construction, the catheter has the conventional form of a patient insertion shaft 33 with a drainage lumen 33c and drainage eye 33c', and connecting with a drainage arm 35, the catheter further having a branch arm 37 which is conventionally utilized for other fluid passage such as the passage of inflation fluid through a lumen 33a to and from a balloon section 33b spaced from the forward tip end 33f of the catheter shaft 33. Conventionally, the catheter is formed of soft latex rubber or other suitable soft, flexibly limber material, thereby providing a problem in packaging of the catheter so as to retain the shaft 33 in a desired generally straight condition from the time of packaging to the time of use. The present invention facilely enables such a packaging and handling of the catheter 31.

Tube sheath 21 is formed of material which is relatively rigid as compared to the highly flexible and bendable soft latex rubber insertion shaft 33 of the catheter 31. It is desirable that the material be selected for the tube sheath 21 such that the tube sheath will self-retain and restore its own cylindrical tube form, yet be sufficiently elastically flexible to enable subsequent pinching of the tube shaft for control during removal of the catheter shaft 33 from the tube sheath, as will be later discussed. To this end, it has been found that a suitable material for the tube sheath 21 is extruded polyethylene tubing. As an example, a catheter having a shaft 13 of ¼ inch O.D. has been assembled in a tube sheath of extruded polyethylene having an I.D. of approximately 9/32 inch, and a wall thickness of approximately 0.02–0.03 inch. The particular thickness, diameter, and clearance are not critical, so long as the desired rigidity is provided for a given tube sheath material, and provided that such clearance is provided between the catheter shaft and the inside of the tube sheath to enable the desired control and ease of assembly and disassembly of the catheter relative to the tube sheath. It is desirable that the tube sheath be translucent or transparent, as this provides aesthetic appeal to the overall package, although in some instances the tube sheath may, if desired, be formed of opaque or relatively opaque and/or colored material.

Tube sheath 21 is sealed across its free end, as by a transverse thermoplastic heat seal bond 25, which may be suitably effected as by a heated jaw clamp or by heated pressure rolls, or otherwise as may be desired. The closing of this end of tube sheath 21 aids in preventing the entry of foreign particles or other contaminant into the tube interior and preventing exit of material from within the tube, being of particular value in enabling the facile packaging of prelubricated catheters where shaft lubricant may tend to bleed or run to some extent.

The catheter 31 and the tube sheath 21 are disposed within the peripherally sealed pocket of the overpackage 13, with the closed end of the tube 21 adjacent one end of the longitudinal package, and the opposite open end of the tube sheath 21 and the extending arms 15, 17 of the catheter 11 disposed adjacent the opposite closed end of the overpackage 13.

The overpackage 13 preferably takes the form of a sandwich of two peelably separable sheets 15, 17. The two sheets 15, 17 may be suitably formed respectively of a gas permeable paper base sheet 15 and a cover sheet 17 of interbonded mylar and polyethylene layers. The mylar-polyethylene cover sheet 17, which is preferably transparent except for such printing as may be placed thereon may itself be a bonded sandwich of an outer layer of mylar and a bottom layer of polyethylene, so as to provide the benefit of both materials, including the strength of mylar and the thermoplastic bonding and ease of sheet handling of polyethylene.

Prior to assembly of the catheter 31 and tube sheath 21 with the overpackage 13, the overpackage may be and is preferably partially pre-formed, by thermoplastic or other suitable peripheral bonding of the plastic cover sheet 17 to the paper base sheet 15, as indicated generally at 17a, preferably employing spaced multiple parallel seal lines to aid in preventing bacterial tunneling, and thereby providing a longitudinally extending central pocket sealed on three sides and with an open unsealed end at one longitudinal end of the dual-sheet overpackage. The assembled catheter 31 and tube sheath 21 may then inserted through the open end of the pocket, to the position as shown in FIG. 1, and thereupon the previously open end may be sealed shut, as indicated at 17a', as by heat-sealing (preferably also multiple line spaced heat seals) of the thermoplastic cover sheet 17 to the paper base sheet 15 across this entire end. The entire package assembly 11, 21, 31 may then be subjected to gas sterilization, and if desired sterilization steps may be effected prior to or after various ones of the preceding assembly operations.

The peripheral seal zone of the overpackage 13, as provided by the seal lines 17a, 17a', provides an unsealed end flap zone 15b, 17b which may be easily separated and pulled apart as indicated at 15b', 17b' to peel the two sheets apart (note FIG. 1, in which the cover sheet is shown in phantom lines partially peeled away from the base sheet 17) and expose the catheter 31 and the tube sheath 21 for removal from the pocket 13a of the overpackage 13.

Upon peeling of the two sheets 15 and 17 apart, the operator may thereupon grasp the tube sheath 21 and remove the tube sheath and catheter assembly, preparatory to operator insertion of the tube sheath into a patient. In removing the catheter 31 from the tube sheath 21, the operator may proceed as illustrated in FIG. 5, grasping tube sheath 21 adjacent its open end with the normally contaminated gloved hand of the operator, while initially grasping the extended and exposed arm section 35, 37 with the opposite sterile gloved hand. In this respect, it will be appreciated that in the course of preparing the patient for catheterization the operator will have normally contaminated one gloved hand while leaving the other gloved hand sterile. The catheter 31 is then withdrawn from the open end of the sheath 21, and the operator may readily control this withdrawal by pinching the tube 21 to a desired extent, as indicated at 21p in FIG. 5, the catheter being indicated by broken lines in the process of being withdrawn from the tube sheath 21, and in full lines in a typical withdrawn position. Thus, a desired frictional retarding force is exerted on the catheter shaft 33 to prevent the shaft from uncontrollably and undesirably slipping out of the tube sheath 21 and striking a foreign object or falling on the floor prior to or while wrapping of the shaft about the fingers of the operator to a position as shown in full lines in FIG. 5, preparatory to further manipulation of the catheter by the operator for insertion of the tip end 33f into a patient. After insertion of the shaft 33 into a patient the operator may then inflate the retention balloon 33b, as by inserting an inflation syringe 5, of conventional construction, into the inflation arm 37 and pumping fluid through arm 37 and lumen 33a to the balloon 33b. It will of course be apparent that the catheter 31 may be of any desired type or construction, and that the present illustration of a Foley-type catheter and inflation syringe 5 for use therewith is only by way of illustration of a typically packaged catheter according to the invention. Also, while one might package a syringe 5 with a catheter, such is not normally desirable, as the syringe may be reusable, whereas it is now the better practice to employ catheters on a single use basis.

Figure 6:
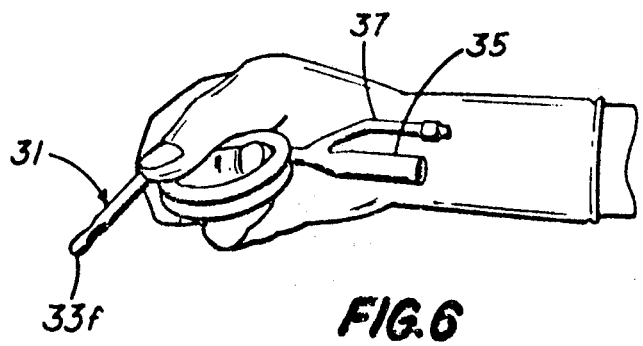
FIG. 6 illustrates a further manipulated position of the catheter preparatory to patient insertion.

From the foregoing discussion it will be apparent that through the employment of the novel catheter packaging arrangement according to this invention, a total packaging arrangement 11 is provided which facilitates assembling of the catheter within the outer overpackage, which maintains the catheter in a generally straight condition from point of packaging to end use, which provides protection for the sterile catheter shaft in case of undetected puncture of the outer overpackage 13, which facilitates the catheter removal from the outer package and subsequent handling of the catheter, such as illustrated in FIG. 6, preparatory to final operator insertion. In addition, the tube sheath materially aids in reducing the likelihood of lubricant staining of the outer package or bleeding of the lubricant from the shaft of a pre-lubricated shaft catheter through the outer package, thereby also better retaining the initial content of lubricant on the catheter shaft in view of the relatively nonporous and low absorption characteristic of the plastic tube sheath, particularly as compared to the paper sheet 17 forming a portion of the overpackage 13. In addition, the smooth extruded plastic tubular sheath reduces the likelihood of pick-up of fibrous or other foreign particles from the paper sheet 15 of the outer package, or from other fibrous or particle sheet material which may be employed, and particularly as has been employed in prior arrangements where cardboard stiffening insert sheets have been utilized to retain the catheter in some semblance of a desired straight configuration.

While the invention has been illustrated and described with respect to a particular illustrative and preferred embodiment, it will be appreciated that various modifications and improvements can be made without departing from the scope and spirit of the invention. For instance, the overpackage might take other forms than as illustrated, such as with both sheets, 15 and 17, being formed of paper. Accordingly, the invention is not to be limited by the particular illustrative embodiment, but only by the scope of the appended claims.

We claim:

1. A packaged catheter arrangement, comprising
    a flexible rubber catheter having an easily flexible insertion shaft with an insertion tip at one end and having two divergent fluid passage arms,
    a flexible tube sheath, the tubular extent and shape of said tube sheath laterally enveloping and serving to protect the length of said catheter insertion shaft during and subsequent to assembly as a dual component unit of said packaged catheter arrangement, said tube sheath being closed at one end and open at its other end, the interior of said tube sheath being of a size to accommodate said catheter shaft, but insufficient to accommodate said two divergent fluid passage arms, and said catheter insertion shaft being removably disposed within said tube sheath with its insertion tip adjacent said closed end of said tube sheath and having its two divergent fluid passage arms adjacent and extending beyond said open end of said tube sheath.

2. A packaged catheter arrangement according to claim 1, one of said divergent fluid passage arms being an inflation arm disposed adjacent and extending beyond said open end of said tube sheath.

3. A packaged catheter arrangement according to claim 1, said closed other end of said tube sheath having a heat seal crimp extending transversely thereof.

4. A packaged catheter arrangement according to claim 1, said catheter insertion shaft being coated with a lubricating medium, and said coated insertion shaft being enclosed within said tube sheath.

5. A packaged catheter arrangement according to claim 1, said catheter having a further fluid conducting arm extending beyond said tube sheath.

6. a packaged catheter arrangement according to claim 1, and a flexible overpackage surrounding said entire catheter and tube sheath and being closed therearound.

7. A packaged catheter arrangement according to claim 6, said flexible overpackage comprising a base of fibrous sheet material and a cover sheet of light-transmitting see-through plastic peripherally bonded to said base sheet about said catheter and tube sheath to form an enclosed loose pocket or cavity for said catheter and tube sheath, said cover sheet being removably peelably separable from said base sheet, and said sheets having unbonded tab ends at one end of said overpackage for ease in separating said sheets to remove said catheter and tube sheath therefrom.

8. a packaged catheter arrangement according to claim 7, said sheets having a peripheral heat seal bond.

9. A packaged catheter arrangement according to claim 1, said flexible tube sheath being substantially more rigid than said catheter insertion shaft and serving the dual function of protecting and rigidifying the length of said insertion shaft and presenting said two divergent passage arms in open accessible extended relation beyond the adjacent open end of said tube sheath.

* * * * *